United States Patent
Miyagawa (10) Patent No.: US 8,145,438 B2
(45) Date of Patent: Mar. 27, 2012

(54) METHOD FOR QUANTITATING SUBSTANCE TO BE MEASURED

(75) Inventor: Haruhiko Miyagawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 415 days.

(21) Appl. No.: 12/444,670

(22) PCT Filed: Oct. 31, 2006

(86) PCT No.: PCT/JP2006/321757
§ 371 (c)(1),
(2), (4) Date: Apr. 7, 2009

(87) PCT Pub. No.: WO2008/053530
PCT Pub. Date: May 8, 2008

(65) Prior Publication Data
US 2010/0100335 A1  Apr. 22, 2010

(51) Int. Cl.
*G01N 31/00* (2006.01)
*G01D 18/00* (2006.01)
(52) U.S. Cl. ...................... 702/23; 250/252.1
(58) Field of Classification Search .............. 702/23–25, 702/27, 81, 84–85, 127, 129, 137, 182–183, 702/189; 73/23.2, 23.22, 23.28, 23.35, 23.37, 73/23.39, 23.41, 24.05, 30.01; 250/252.1, 250/281–283, 288
See application file for complete search history.

(56) References Cited

FOREIGN PATENT DOCUMENTS

| JP | 09-133685 A | 5/1997 |
|---|---|---|
| JP | 2001-337080 A | 12/2001 |
| JP | 2003-139755 A | 5/2003 |
| JP | 2004-061485 A | 2/2004 |
| JP | 2006-138786 A | 6/2006 |

OTHER PUBLICATIONS

Kitakyushu Foundation, Method for Simultaneous Identification and Quantitative Determination for Widely Used Multi-Component in Chromatography/Mass Spectrograph, JP 2003-139755 A (English translation version), May 14, 2003, 5 pp.*

Nakagawa et al., Determination of Pesticides Using Negative Chemical Ionization Gas Chromatography-Mass Spectrometry, 2001, Analytical Sciences, vol. 17 Supplment, The Japan Society for Analytical Chemistry, pp. i883-i884.*

\* cited by examiner

*Primary Examiner* — Michael Nghiem
*Assistant Examiner* — Toan M Le
(74) *Attorney, Agent, or Firm* — Sughrue Mion, PLLC

(57) ABSTRACT

A method for quantitating a substance to be measured including: storing a database with which a relative calibration curve is registered; measuring an internal standard substance having a known concentration; calculating the peak area or the height of an internal standard substance by preparing a chromatogram on the basis of a mass spectrum of the internal standard substance; gaining a mass spectrum of the substance to be measured by measuring the substance; calculating the peak area or the height of the substance by preparing a chromatogram on the basis of the mass spectrum of the substance to be measured; and calculating the concentration of the substance on the basis of the relative calibration curve, the peak area or the height of the internal standard substance and the peak area or the height of the substance.

4 Claims, 5 Drawing Sheets

METHOD FOR QUANTITATING SUBSTANCE TO BE MEASURED

TECHNICAL FIELD

The present invention relates to a method for quantitating substance to be measured, and in particular, to a method for quantitating substance to be measured according to which a substance to be measured is quantitated using a chromatographic mass spectrometer.

BACKGROUND TECHNOLOGY

Gas chromatographic mass spectrometers (GC/MS) are formed of a gas chromatographic apparatus and a mass spectrometer. As a result, first, substances to be measured included in a substance (sample) that is the object of analysis are separated along the time axis in a gas chromatographic apparatus (GC). Next, the respective substances to be measured separated along the time axis are measured using a mass spectrometer (MS) so that the substances to be measured are separated according to the mass number so as to be detected. This measurement is repeated with short time intervals so that a number of mass spectra having the mass number along the lateral axis and the ion intensity along the longitudinal axis are prepared. In addition, the peak of a certain mass number is focused for each of the mass spectra, and the focused peaks are aligned along the time axis so that a mass chromatogram is prepared. Furthermore, all the peaks appearing in one mass spectrum are integrated, and they are aligned along the time axis so that a total ion chromatogram is prepared.

Thus, the substance to be measured is quantitated on the basis of the area and the height of the peaks appearing in this mass chromatogram and the total ion chromatogram. At this time, a standard substance of which the concentration is known in advance is introduced into a GC/MS in order to carry out quantification, and the calibration curve, which is prepared on the basis of the relationship between the gained peak area or height and the concentration as a result of the measurement, is used.

Figure 3:
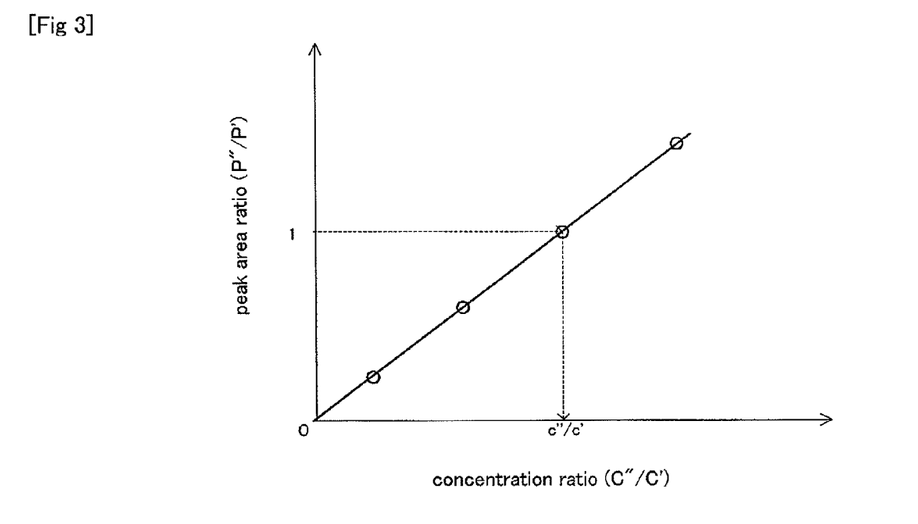
FIG. 3 shows a relative calibration curve indicating the relationship between the peak area ratio in the chromatograph of the standard substance to the internal standard substance and the concentration ratio of the standard substance to the internal standard substance.

It is necessary, however, to measure a standard substance under certain conditions for measurement in order to prepare a calibration curve for every GC/MS apparatus. Therefore, a method for identifying and quantitating multiple components for general purposes in a GC/MS according to which a substance to be measured can be quantitated irrespective of the GC/MS used is disclosed (see, for example, Patent Document 1). This method for identifying and quantitating multiple components for general purposes collectively includes the database storing step of storing a database with which a relative calibration curve indicating the relationship between the peak area ratio in the chromatogram for the standard substance and the internal standard substance and the concentration ratio of the standard substance to the internal standard substance is registered (see FIG. 3), the measurement step of measuring an internal standard substance of which the concentration is known and a substance to be measured at the same time so that the mass spectra of the internal standard substance and the substance to be measured are gained, the calculation step of calculating the peak area ratio of the substance to be measured to the internal standard substance by preparing a chromatograph on the basis of the mass spectrum of the internal standard substance having a predetermined concentration and the mass spectrum of the substance to be measured, and the substance to be measured concentration calculating step of calculating the concentration of the substance to be measured on the basis of a relative calibration curve.

In accordance with this method for quantitating a substance to be measured, the concentration of the substance to be measured can be calculated using a relative calibration curve on the basis of the peak area ratio of the substance to be measured to the internal standard substance that is measured at the same time as the substance to be measured, and therefore, it is not necessary to prepare a calibration curve in advance by measuring the standard substance under certain conditions for measurement for every GC/MS used.

Here, the internal standard substance is selected from stable isotope compounds and compounds having similar chemical and physical properties of which the response to a GC/MS is similar to that of the substance to be measured and which can be measured separately from the substance to be measured. Deuterium bodies (D bodies), where hydrogen atoms are substituted with deuterium atoms, can be cited as examples.

In addition, chemicals substances including environment polluting substances, such as PCB, residual pesticides in foods and misused chemicals, can be cited as the standard substance.

Patent Document 1: Japanese Unexamined Patent Publication 2003-139755

DISCLOSURE OF THE INVENTION

Problem to be Solved by the Invention

In accordance with the above described method for quantitating a substance to be measured, however, an internal standard substance must be prepared for each sample in the case where a great number of samples are measured, and therefore, a great amount of internal standard substances must be prepared, and it takes time and effort to add an internal standard substance to each sample.

In addition, internal standard substances are generally expensive and some types are difficult to secure, and thus, in some cases it is difficult to use the above described quantitating method.

Thus, an object of the present invention is to provide a method for quantitating a substance to be measured where the amount of the internal standard substances and the frequency of use can be reduced in the case where a great number of samples are measured.

Means for Solving Problem

The method for quantitating a substance to be measured according to the present invention in order to solve the above described problems is a method for quantitating a substance to be measured according to which a substance to be measured is quantitated using a chromatographic mass spectrometer, and includes: a database storing step of storing a database, with which a relative calibration curve is registered showing the relationship between a peak area ratio or a height ratio in the chromatogram of a standard substance to a registered substance and the concentration ratio of the standard substance to the registered substance; an internal standard substance measuring step of measuring an internal standard substance having a known concentration so that a mass spectrum of the internal standard substance is gained; an absolute value calculating step of calculating the peak area or the height of an internal standard substance by preparing a chromatogram on the basis of the mass spectrum of the internal standard substance; a substance to be measured measuring step of gaining a mass spectrum of the substance to be measured by measuring the substance to be measured; a measured value calculating step of calculating the peak area or the height of the substance to be measured by preparing a chromatogram on the basis of the mass spectrum of the substance to be measured; and a concentration of a substance to be measured calculating step of calculating the concentration of the substance to be measured on the basis of the relative calibration curve, the peak area or the height of the internal standard substance and the peak area or the height of the substance to be measured.

According to the method for quantitating a substance to be measured according to the present invention, first, a relative calibration curve showing the relationship between the peak area ratio or the height ratio in the chromatogram of the standard substance to the registered substance and the concentration ratio of the standard substance to the registered substance is stored. Next, only the internal standard substance having a known concentration is measured under certain conditions for measurement in the GC/MS used, and thus, the peak area or the height of the internal standard substance in the GC/MS used is calculated. At this time, the same substance is used for the registered substance and the internal standard substance. After that, the substance to be measured is measured for a sample to which no internal standard substance is added using the GC/MS, and thus, the peak area or the height of the substance to be measured is calculated. As a result, the concentration of the substance to be measured can be calculated on the basis of the relative calibration curve, the peak area or the height of the internal standard substance, and the peak area or the height of the substance to be measured. Accordingly, the internal standard substance is used once or a few times instead of for every sample. As a result, the amount of the internal standard substance and the frequency of use can be reduced.

Furthermore, in the case where the internal standard substance negatively affects the human body, these effects can be reduced because the amount of the internal standard and the frequency of use are low.

Means for Solving Other Problems and Working Effects

In addition, in accordance with the method for quantitating a substance to be measured according to the present invention, an absolute calibration curve showing the relationship between the peak area or the height and the concentration may be prepared on the basis of the relative calibration curve and the peak area or the height of the internal standard substance.

In addition, in accordance with the method for quantitating a substance to be measured according to the present invention, the above described registered substance may be a deuterium body where hydrogen atoms are substituted with deuterium atoms, and no hydrogen atoms may be substituted with deuterium atoms in the above described internal standard substance.

In accordance with the method for quantitating a substance to be measured according to the present invention, the substance to be measured can be measured without adding the internal standard substance to the sample, and therefore, it is not necessary to use the substance to be measured that can be measured separately as an internal standard substance. That is to say, it becomes unnecessary to use an expensive deuterium body (D body).

EXPLANATION OF SYMBOLS 1 gas chromatograph apparatus (GC)
5 mass spectrometer (MS)
11 CPU (data processing unit)
12 memory (external storing unit)
20 computer
21 measuring portion
22 area calculating portion
23 absolute calibration curve preparing portion
24 substance to be measured calculating portion
100 gas chromatographic mass spectrometer

BEST MODE FOR CARRYING OUT THE INVENTION

In the following, the embodiments of the present invention are described in reference to the drawings. Here, the present invention is not limited to the following embodiments, and needless to say, various modifications may be included within the scope, provided that they do not deviate from the gist of the present invention.

Figure 1:
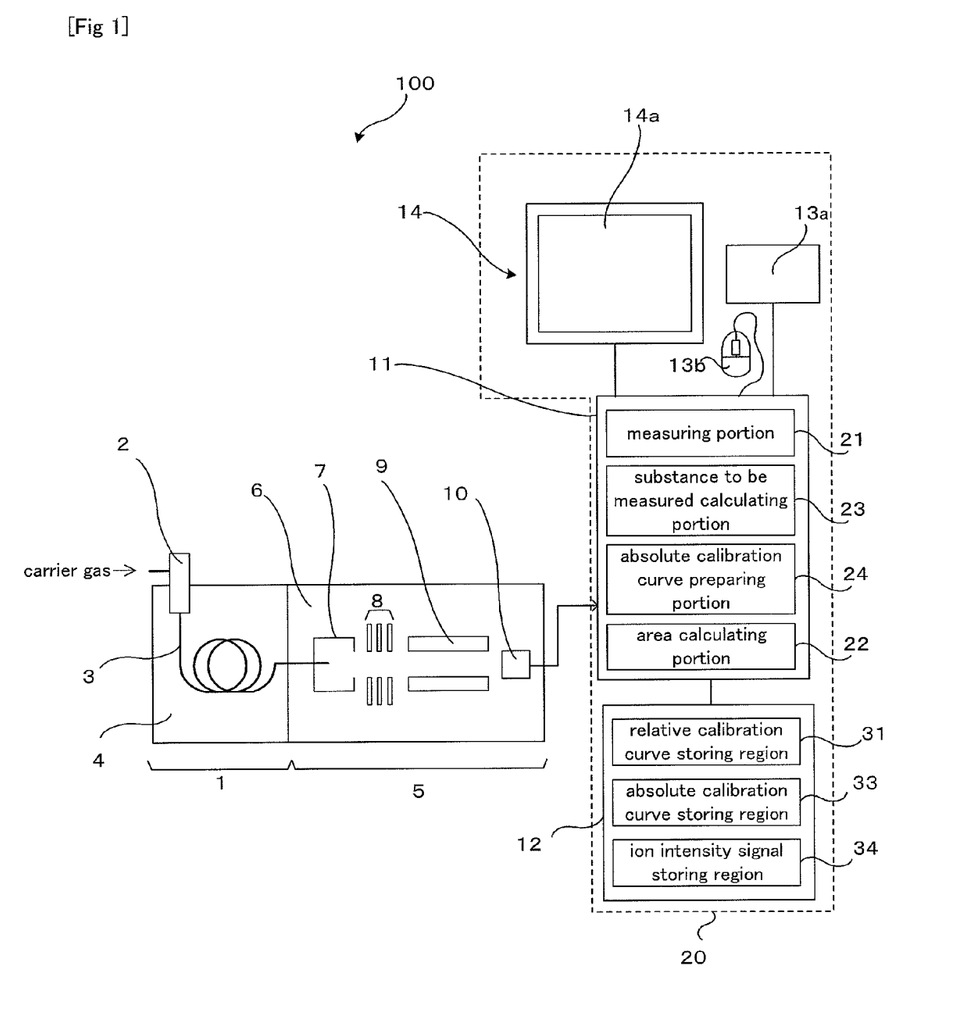
FIG. 1 is a diagram showing the configuration of a GC/MS apparatus where the method for quantitating a substance to be measured according to the present invention is used.

FIG. 1 is a diagram showing the configuration of a GC/MS apparatus where the method for quantitating a substance to be measured according to the present invention is used. The GC/MS apparatus is made up of a GC 1, an MS 5 and a computer 20.

The GC 1 is made up of a column oven 4, a column 3 contained within the column oven 4, and a sample injecting portion 2 connected to an entrance end of the column 3. The GC 1 is made up of a column oven 4, a column 3 contained within the column oven 4 and a sample injecting portion 2 connected to an entrance end of the column 3. A sample gas (sample), which is the object of analysis, is introduced into the column 3 from the sample injecting portion 2 when pushed by a carrier gas. As a result, the respective substances to be measured included in the sample gas are separated along the time axis while passing through the column 3, and reach the exit end of the column 3. Here, the exit end of the column 3 is connected to the MS 5.

The MS 5 is provided with an ion source 7 that is connected to the exit end of the column 3, an ion lens 8, a quadrupole filter 9 to which a voltage is applied, and a detector 10, within an analysis chamber 6 from which air is discharged so that the inside becomes a vacuum. The respective substances to be measured which flow out from the column 3 in sequence are ionized in the ion source 7 as a result of collision with electrons or chemical reaction. Consequently, the generated ions fly out from the ion source 7 so as to be condensed by the ion lens 8 and accelerate appropriately, and after that introduced into the space of the quadrupole filter 9 in the longitudinal direction.

Only ions having a mass number (mass m/charge z) in accordance with the applied voltage pass through the quadrupole filter 9 to which a voltage gained when a direct current voltage and a high frequency voltage overlap is applied, and thus, selected ions reach the detector 10. At this time, the mass number of ions that pass through the quadrupole filter 9 depends on the applied voltage, and therefore, an ion intensity signal for ions having a predetermined mass number can be gained in the detector 10 by scanning the applied voltage. Here, the output of the detector 10 is inputted into the computer 20.

The computer 20 is provided with a CPU (data processing unit) 11, and in addition, a memory (external storing unit) 12, a keyboard 13*a* and a mouse 13*b*, which are input units, and a display 14 having a monitor screen 14*a* are connected to the computer.

The function in terms of the processing of the CPU 11 is illustrated as blocks when a measuring portion 21, an area calculating portion 22, an absolute calibration curve generating portion 23 and a substance to be measured calculating portion 24 are provided. The measuring portion 21 stores the ion intensity signal acquired by the detector 10 in an ion intensity signal storing region 34 in the memory 12, and at the same time, carries out an arithmetic operation on the basis of the ion intensity signal and outputs the results to the monitor screen 14*a*.

In addition, the memory 12 has a relative calibration curve storing region 31 with which a relative calibration curve indicating the relationship between the peak area ratio of the standard substance to the registered substance in the total ion chromatogram and the concentration ratio of the standard substance to the registered substance, an absolute calibration curve storing region 33 which stores an absolute calibration curve, and an ion intensity signal storing region 34.

The measuring portion 21 prepares a mass spectrum by taking the ion intensity when mass scanning is carried out for a certain retention time along the longitudinal axis and the mass number along the lateral axis, for example. Mass scanning can be intermittently repeated in sequence at constant intervals, so that a great number of mass spectra can be acquired in correspondence to the respective substances to be measured, which flow out in sequence from the column 3. In addition, after acquiring this mass spectrum, a mass chromatogram can be gained by focusing on a certain mass number and spreading the ion intensity along the time axis so as to sample the ion intensity. Furthermore, whenever a mass spectrum is acquired, the sum of the ion intensity is calculated and spread along the time axis so as to sample it, and as a result, a total ion chromatogram can be gained.

The area calculating portion 22 finds out a peak of the substance to be measured or the internal standard substance in this mass chromatogram or total ion chromatogram and controls the calculation of the peak area of the substance to be measured or the internal standard substance. At this time, the amount of inclination of the curve of the total ion chromatogram is checked in sequence, for example, so that it is determined that the point where the amount of inclination becomes a predetermined value or greater is the starting point of the peak, it is determined that the point where the amount of inclination turns from 0 to a negative is the top of the peak, and it is determined that the point where the amount of inclination becomes a predetermined value or greater is the end point of the peak. When the peak is specified in the total ion chromatogram as described above, the area of the peak is calculated (see FIG. 2).

Figure 4:
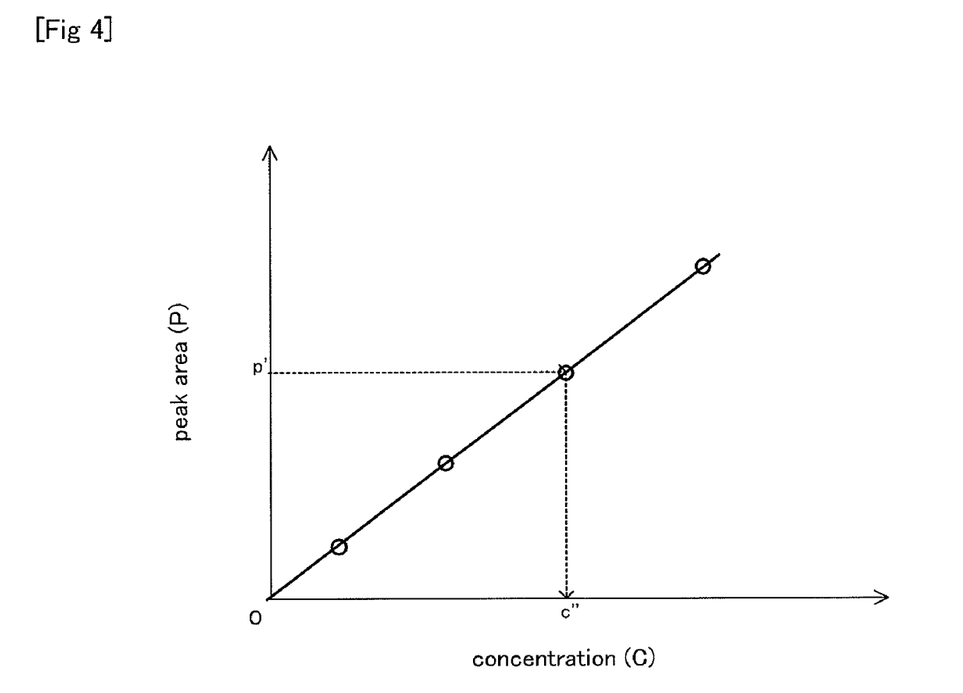
FIG. 4 shows an absolute calibration curve indicating the relationship between the peak area or the height and the concentration.

The absolute calibration curve generating portion 23 generates an absolute calibration curve which is used when a substance to be measured is quantitated on the basis of the relative calibration curve and the peak area of the internal standard substance and controls the storage in the absolute calibration curve storing region 33. Here, the "relative calibration curve" can be used for every GC/MS due to the relationship in the mass spectrum between the internal standard substance and the substance to be measured. Meanwhile, the "absolute calibration curve" can be used only for the GC/MS apparatus 100 due to the mass spectrum of only the substance to be measured. Therefore, an absolute calibration curve showing the relationship between the peak area and the concentration in the GC/MS apparatus 100 used (see FIG. 4) is prepared from the relative calibration curve showing the relationship between the peak area ratio of the standard substance to the registered substance in the total ion chromatogram and the concentration ratio of the standard substance to the registered substance (see FIG. 3) with the method for generating an absolute calibration curve being described below. As a result, a substance to be measured can be quantitated without the inner standard substance being added to each sample.

The substance to be measured calculating portion 24 controls the quantitation of the substance to be measured on the basis of the absolute calibration curve and the peak area of the substance to be measured.

Figure 5:
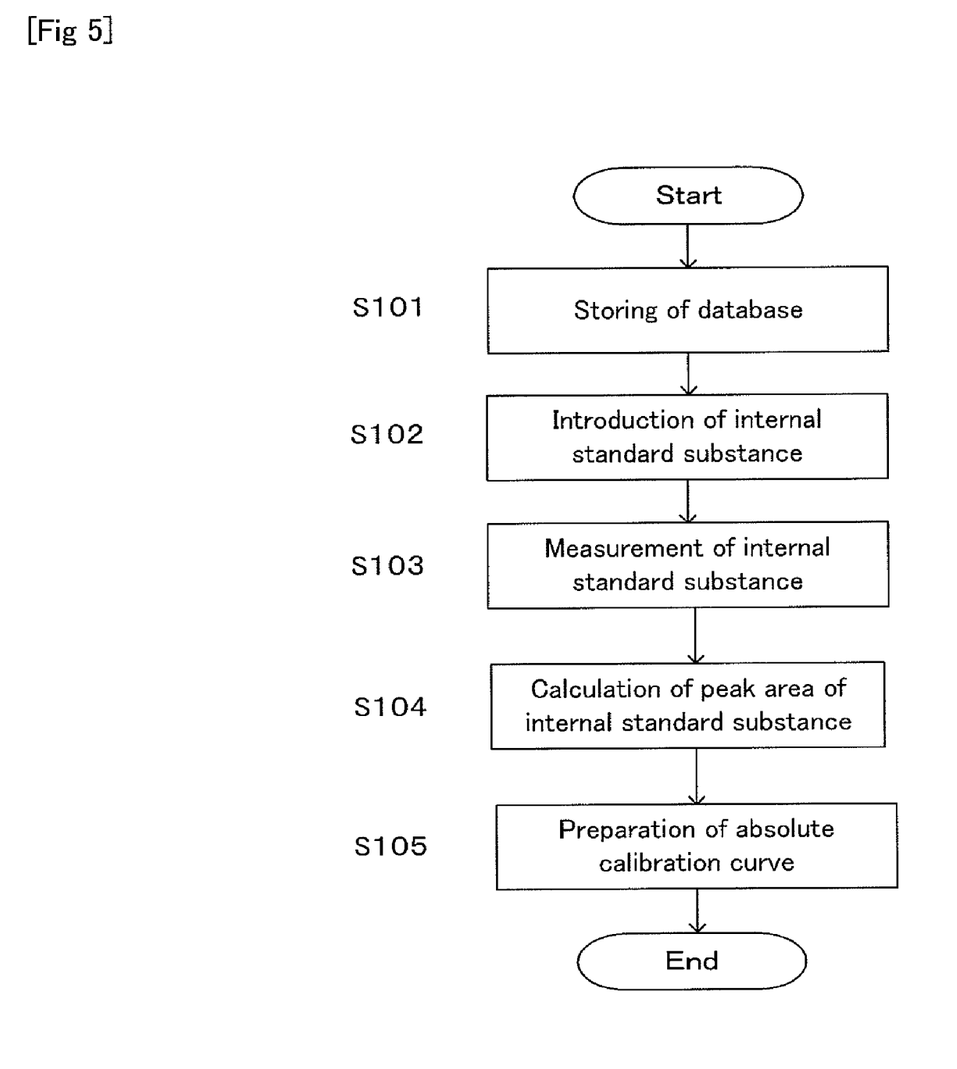
FIG. 5 is a flow chart showing the procedure in accordance with the method for preparing an absolute calibration curve.

Here, the method for generating an absolute calibration curve, according to which an absolute calibration curve is generated, is described. FIG. 5 is a flow chart showing the procedure of the method for generating an absolute calibration curve.

First, in the process in the step S101, a database with which a relative calibration curve (see FIG. 3) showing the relationship between the peak area ratio (P"/P') of the standard substance to the registered substance in the total ion chromatogram and the concentration ratio (C"/C') of the standard substance to the registered substance is registered is stored in the relative calibration curve storing region 31 (database storing step). Here, P" is the peak are of the standard substance, P' is the peak area of the registered substance, C" is the concentration of the standard substance, and C' is the concentration of the registered substance.

Next, in the process in the step S102, a constant amount of a sample gas (sample) containing an internal standard substance having an already known concentration (c') is introduced into the column 3 from the sample injecting portion 2. At this time, the registered substance and the internal standard substance used are the same.

Next, in the process in the step S103, mass scanning is intermittently repeated in sequence with constant intervals, and thus, a mass spectrum of the internal standard substance is gained (internal standard substance measuring step).

Figure 2:
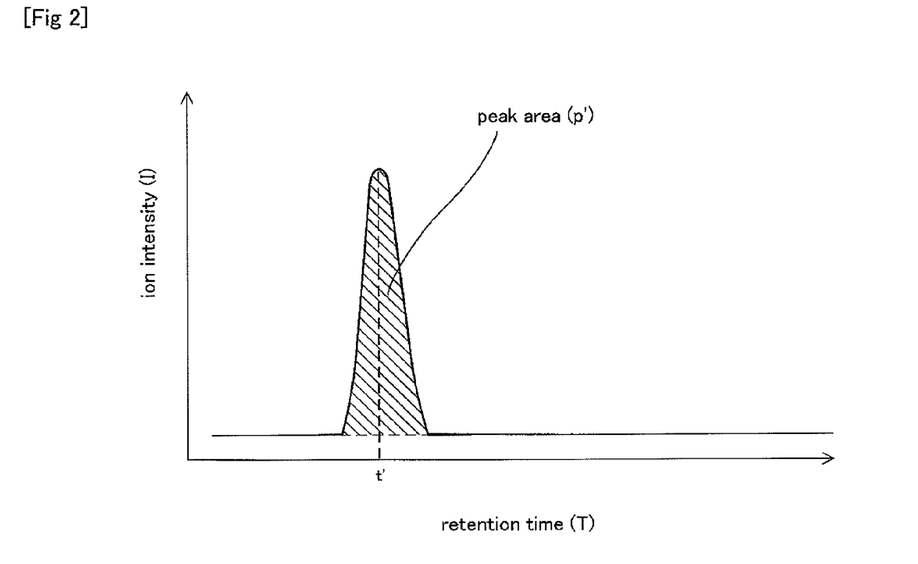
FIG. 2 is a total ion chromatogram prepared on the basis of the mass spectrum of the internal standard substance.

Next, in the process in the step S104, a total ion chromatogram is prepared on the basis of the mass spectrum of the internal standard substance, and thus, the peak area of the internal standard substance (p') is calculated (absolute value calculating step). As shown in FIG. 2, for example, the peak area (p') of the concentration (c') of the internal standard substance is gained.

Next, in the process in the step S105, an absolute calibration curve showing the relationship between the peak area (P) and the concentration (D) in the GC/MS apparatus 100 used is generated on the basis of the relative calibration curve and the peak area (p') of the internal standard substance so as to be stored in the absolute calibration curve storing region 33. First, the longitudinal axis of the relative calibration curve indicates the peak area ratio (P"/P') of the standard substance to the registered substance, and therefore, is converted to the peak area (P), for example. P"/P'=1 is converted to p' and P"/P'=2 is converted to 2p', for example. Next, the lateral axis of the relative calibration curve indicates the concentration ratio (C"/C') of the standard substance to the registered substance, and therefore, is converted to the concentration (D). When the longitudinal axis after the conversion is p', for example, conversion is carried out such that the concentration of the standard substance when P"/P'=1 before the conversion becomes c".

After that, the process in the step S105 is completed, and thus, the present flow chart is completed.

Figure 6:
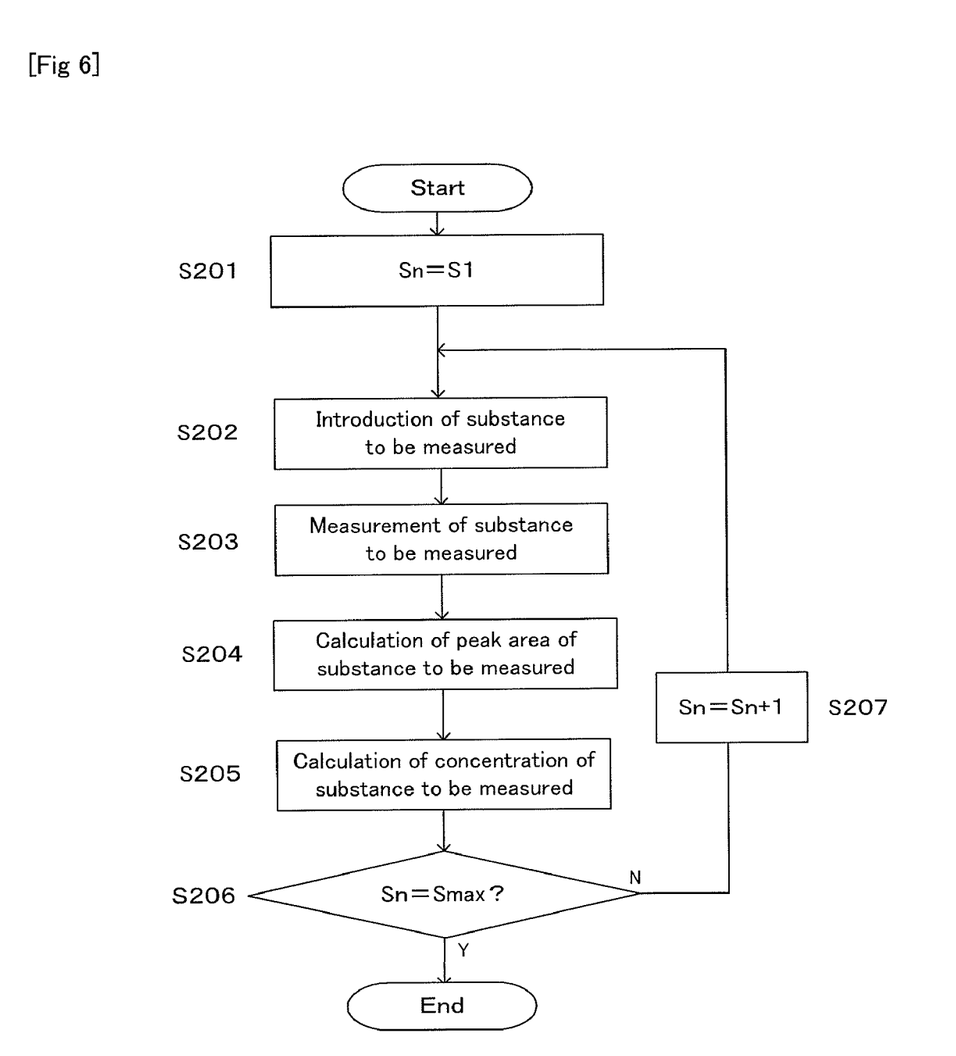
FIG. 6 is a flow chart showing the procedure in accordance with a method for quantitation.

Next, a quantitating method for quantitating a substance to be measured is described. FIG. 6 is a flow chart showing the procedure of the quantitating method. Here, Smax samples are examined.

First, in the process in the step S201, Sn=S1 is stored using a counter Sn.

Next, in the process in the step S202, a constant amount of a sample gas (sample), which is the object of analysis, is introduced into the column 3 from the sample injecting portion 2. At this time, no internal standard substance is added to the sample.

Next, in the process in the step S203, mass scanning is intermittently repeated in sequence with constant intervals, and thus, a mass spectrum of each substance to be measured is gained (substance to be measured measuring step).

Next, in the process in the step S204, a total ion chromatogram is prepared on the basis of the mass spectrum of each substance to be measured, and thus, the peak area (p) of each substance to be measured is calculated (measured value calculating step).

Next, in the process in the step S205, the concentration (c) of the substance to be measured is calculated on the basis of the absolute calibration curve (concentration of substance to be measured calculating step).

Next, in the process in the step S206, whether or not Sn=Smax is determined. When it is determined that Sn=Smax is not true, Sn=Sn+1 is stored in the process in the step S207 and the procedure returns to the process in the step S202. That is to say, the processes in the steps S202 to S205 are repeated until it is determined that Sn=Smax.

Meanwhile, in the case where it is determined that Sn=Smax, the present flow chart is completed.

As described above, in accordance with the method for quantitating a substance to be measured according to the present invention, first, a relative calibration curve showing the relationship between the peak area ratio (P"/P') of the standard substance to the internal standard substance in the chromatogram and the concentration ratio (C"/C') of the standard substance to the internal standard substance is stored. Next, in the GC/MS apparatus 100, only the internal standard substance having an already known concentration (c') is measured under certain conditions for measurement, and thus, the peak area (p') of the internal standard substance is calculated in the GC/MS apparatus 100. After that, a substance to be measured is measured for a sample to which no internal standard substance is added in the GC/MS apparatus 100, and thus, the peak area (p) of the substance to be measured is calculated. As a result, the concentration (c) of the substance to be measured can be calculated on the basis of the relative calibration curve, the peak area (p') of the internal standard substance and the peak area (p) of the substance to be measured. Accordingly, it is not necessary to set the amounts of the internal standard substance and the frequency of use for each sample, and one amount can be set at once. That is to say, the amount of the internal standard substance and the frequency of use can be reduced, and thus, it is possible to make the quantitating work easy even in the case where the internal standard substance is expensive or is a certain type that is difficult to gain.

Furthermore, the amount of the internal standard substance is small and the frequency of use is low, and therefore, in the case where the internal standard substance negatively affects the human body, the effects can be reduced.

Other Embodiments (1) Though the above described GC/MS apparatus 100 has a configuration where the registered substance and the internal standard substance used are the same, the registered substance may be a deuterium body where hydrogen atoms are substituted with deuterium atoms and the internal standard substance may have no deuterium atoms substituted for hydrogen atoms in the configuration. At this time, the peak area of the internal standard substance=the peak area of the registered substance×A is achieved, where A is a constant.

(2) Though the number of times of measurements of the internal standard substance is one in the above described GC/MS apparatus 100, the internal standard substance may be measured once per ten measurements of the sample in the configuration.

INDUSTRIAL APPLICABILITY

The present invention can be used in methods for quantitating a substance to be measured according to which a substance to be measured is quantitated in a GC/MS.

The invention claimed is:

1. A method for quantitating a substance to be measured, according to which a substance to be measured is quantitated using a chromatographic mass spectrometer, comprising:
   a database storing step of storing a database, with which a relative calibration curve is registered showing the relationship between a peak area ratio or a height ratio in the chromatogram of a standard substance to a registered substance and the concentration ratio of the standard substance to the registered substance;
   an internal standard substance measuring step of measuring an internal standard substance having a known concentration by selecting the same substance as said registered substance as the internal standard substance or selecting a substance having no deuterium atoms substituted for hydrogen atoms as the internal standard substance when said registered substance is a deuterium body where hydrogen atoms are substituted with deuterium atoms so that a mass spectrum of the internal standard substance is gained;
   an absolute value calculating step of calculating the peak area or the height of an internal standard substance by preparing a chromatogram on the basis of the mass spectrum of the internal standard substance by a processor;
   a substance to be measured measuring step of gaining a mass spectrum of the substance to be measured by measuring the substance to be measured of which the concentration is unknown;
   a measured value calculating step of calculating the peak area or the height of the substance to be measured by preparing a chromatogram on the basis of the mass spectrum of the substance to be measured by the processor; and a concentration of a substance to be measured calculating step of calculating the concentration of the substance to be measured on the basis of the relative calibration curve, the peak area or the height of the internal standard substance and the peak area or the height of the substance to be measured by the processor.

2. The method for quantitating a substance to be measured according to claim 1, characterized in that said registered substance is a deuterium body where hydrogen atoms are substituted with deuterium atoms, and the hydrogen atoms are not substituted with deuterium atoms in said internal standard substance.

3. A method for quantitating a substance to be measured, according to which a substance to be measured is quantitated using a chromatographic mass spectrometer, comprising:

a database storing step of storing a database, with which a relative calibration curve is registered showing the relationship between a peak area ratio or a height ratio in the chromatogram of a standard substance to a registered substance and the concentration ratio of the standard substance to the registered substance;

an internal standard substance measuring step of measuring an internal standard substance having a known concentration by selecting the same substance as said registered substance as the internal standard substance or selecting a substance having no deuterium atoms substituted for hydrogen atoms as the internal standard substance when said registered substance is a deuterium body where hydrogen atoms are substituted with deuterium atoms so that a mass spectrum of the internal standard substance is gained;

an absolute value calculating step of calculating the peak area or the height of an internal standard substance by preparing a chromatogram on the basis of the mass spectrum of the internal standard substance by a processor;

a substance to be measured measuring step of gaining a mass spectrum of the substance to be measured by measuring the substance to be measured of which the concentration is unknown;

a measured value calculating step of calculating the peak area or the height of the substance to be measured by preparing a chromatogram on the basis of the mass spectrum of the substance to be measured by the processor; and a concentration of a substance to be measured calculating step of calculating the concentration of the substance to be measured by generating an absolute calibration curve showing the relationship between the peak area or the height and the concentration on the basis of the relative calibration curve and the peak area or the height of the internal standard substance, and then by substituting the peak area or the height of said substance to be measured for the peak area or the height in said absolute calibration curve by the processor.

4. The method for quantitating a substance to be measured according to claim 3, characterized in that said registered substance is a deuterium body where hydrogen atoms are substituted with deuterium atoms, and the hydrogen atoms are not substituted with deuterium atoms in said internal standard substance.

* * * * *